US005599535A

United States Patent [19]
Polansky et al.

[11] Patent Number: 5,599,535
[45] Date of Patent: *Feb. 4, 1997

[54] METHODS FOR THE CYTO-PROTECTION OF THE TRABECULAR MESHWORK

[75] Inventors: Jon R. Polansky, Mill Valley; Ernest Bloom, Alamo; Donald J. Fauss, San Francisco, all of Calif.

[73] Assignee: Regents of the University of California, Oakland, Calif.

[ * ] Notice: The term of this patent shall not extend beyond the expiration date of Pat. No. 5,474,985.

[21] Appl. No.: 479,185

[22] Filed: Jun. 7, 1995

[51] Int. Cl.$^6$ .............................. A61K 31/74; A61K 9/70; A61K 9/127; A61F 2/02
[52] U.S. Cl. .................. 424/78.04; 424/423; 424/443; 424/450; 424/451; 424/464; 514/912; 514/913; 514/914; 514/915
[58] Field of Search ................................. 514/912, 913, 514/914, 915; 424/78.04, 423, 443, 450, 451, 464

[56] References Cited

U.S. PATENT DOCUMENTS

| | | | |
|---|---|---|---|
| 2,798,053 | 7/1957 | Brown | 260/2.2 |
| 3,732,865 | 5/1973 | Higuchi et al. | 128/260 |
| 3,773,919 | 11/1973 | Boswell et al. | 424/19 |
| 3,887,699 | 6/1975 | Yolles | 424/19 |
| 4,136,250 | 1/1979 | Mueller et al. | 528/29 |
| 4,192,827 | 3/1980 | Mueller et al. | 525/123 |
| 4,327,725 | 5/1982 | Cortese et al. | 128/260 |
| 4,454,151 | 6/1984 | Waterbury | 424/274 |
| 4,522,826 | 6/1985 | Sunshine et al. | 514/569 |
| 4,543,251 | 9/1985 | Kamishita | 424/81 |
| 4,548,990 | 10/1985 | Mueller et al. | 525/123 |
| 4,617,299 | 10/1986 | Knepper | 514/178 |
| 4,670,254 | 6/1987 | Kamishita | 424/81 |
| 4,690,927 | 9/1987 | Voss et al. | 514/282 |
| 4,711,782 | 12/1987 | Okada et al. | 424/455 |
| 4,711,906 | 12/1987 | von Stetten et al. | 514/561 |
| 4,757,060 | 7/1988 | Lukacsko et al. | 514/169 |
| 4,757,089 | 7/1988 | Epstein | 514/571 |
| 4,777,174 | 10/1988 | Sunshine et al. | 514/264 |
| 4,829,088 | 5/1989 | Doulakas | 514/567 |
| 4,855,293 | 8/1989 | Collington et al. | 514/212 |
| 4,876,250 | 10/1989 | Clark | 514/179 |
| 4,880,742 | 11/1989 | Hayaishi et al. | 435/238 |
| 4,904,649 | 2/1990 | Schwartz | 514/174 |
| 4,917,886 | 4/1990 | Asche et al. | 424/81 |
| 4,948,805 | 8/1990 | Ziggiotti et al. | 514/428 |
| 4,960,799 | 10/1990 | Nagy | 514/567 |
| 4,971,802 | 11/1990 | Tarcsay et al. | 424/450 |
| 4,973,469 | 11/1990 | Mulligan et al. | 424/461 |
| 4,980,170 | 12/1990 | Schneider et al. | 424/451 |
| 4,999,379 | 3/1991 | Fankhauser | 514/567 |
| 5,036,097 | 7/1991 | Floyd et al. | 514/400 |
| 5,110,493 | 5/1992 | Cherng-Chyi et al. | 514/413 |
| 5,124,154 | 6/1992 | Babcock et al. | 424/427 |
| 5,190,762 | 3/1993 | Yarosh | 424/450 |
| 5,192,535 | 3/1993 | Davis et al. | 424/78.04 |
| 5,200,453 | 4/1993 | Janssen | 514/399 |
| 5,270,052 | 12/1993 | Gelfand et al. | 424/450 |
| 5,304,561 | 4/1994 | Faezeh . | |
| 5,314,909 | 5/1994 | Dollerup | 514/420 |
| 5,474,985 | 12/1995 | Polansky et al. | 514/26 |

FOREIGN PATENT DOCUMENTS

| | | |
|---|---|---|
| 1176565 | 10/1984 | Canada . |
| 0058481A1 | 8/1982 | European Pat. Off. . |
| 0133988A2 | 3/1985 | European Pat. Off. . |
| 0158277A2 | 10/1985 | European Pat. Off. . |
| 0160408A1 | 11/1985 | European Pat. Off. . |
| 0306984 | 3/1989 | European Pat. Off. . |
| 0390071A1 | 10/1990 | European Pat. Off. . |
| 0422681A1 | 4/1991 | European Pat. Off. . |
| 0466650A2 | 1/1992 | European Pat. Off. . |
| 0550921A1 | 7/1993 | European Pat. Off. . |
| 58-152811 | 9/1983 | Japan . |
| 62-123119 | 6/1987 | Japan . |
| WO89/06964 | 8/1989 | WIPO . |
| WO91/05771 | 5/1991 | WIPO . |
| WO91/16896 | 11/1991 | WIPO . |
| WO91/19482 | 12/1991 | WIPO . |
| WO92/00044 | 1/1992 | WIPO . |
| WO92/00707 | 1/1992 | WIPO . |
| WO93/12234 | 6/1993 | WIPO . |
| WO94/04557 | 3/1994 | WIPO . |
| WO9509639 | 4/1995 | WIPO . |
| WO9517178 | 6/1995 | WIPO . |

OTHER PUBLICATIONS

Synder, R. W. et al. "Corticosteroid treatment and trabecular meshwork proteases in cell and organ culture supernatents", *Exp. Eye. Res.*, 57:4 461–468 (1993).

Database Pharma Projects, PJB Publications Ltd., Dialog File 928 Accession Nr. 021312, (1996).

Gerritsen et al., "Prostaglandin Synthesis and Release from Cultured Human Trabecular Meshwork Cells and Scleral Fibroblasts". *Exp. Eye. Res.* 43:1089–1102 (1986).

Herbort et al., "Anti–inflammatory Effect of Topical Diclofenac After Argon Laser Trabeculoplasty", *Klin Mbl. Augenheik*, 200:358–361 (1992).

InSite Vision Annual Report (1993).

Polansky, J. R., et al. *In Vitro Studies of Human Trabecular Cells: Perspectives and Limitations*, Proc. Int. Soc. for Eye Research, vol. I, p. 3 (1980).

Polansky, J. R., et al. *Glucocorticoid Receptors and Steroid Glaucoma Mechanisms*, Encounters in Glaucoma Research I: Receptor Biology and Glaucoma, pp. 273–299 (Feb. 1994).

Alvarado, J. A. et al.–*Human Trabecular Cells*, Invest. Ophthalmol. Vis. Sci. 23:464–478 (1982).

Babizhayev, M. A. et al.–*Lipid Peroxidation in Open–angle Glaucoma*, Invest. Ophthalmol. Vis. Sci. 67:371–377 (1989).

(List continued on next page.)

*Primary Examiner*—Carlos Azpuru
*Attorney, Agent, or Firm*—Howrey & Simon

[57] ABSTRACT

The invention concerns the recognition that certain non-steroidal anti-inflammatory agents produce cytoprotective effects on trabecular cells, and thus can be used to prevent injury to the cells and treat the loss of trabecular cells caused by oxidative or other forms of injury to the cells. Such treatment can ameliorate the severity, or prevent, glaucoma.

31 Claims, No Drawings

OTHER PUBLICATIONS

Bengtsson, B.–*Incidence of Manifest Glaucoma*, British J. of Ophthalmology, 73:483–487 (1989).

Bhuyan, K. C. et al.–*Regulation of Hydrogen Peroxide in Eye Humors: Effect of 3–Amino–1H–1,2,4–Triazole on Catalase and Glutathione Peroxidase of Rabbit Eye*, Biochmica et Biophysica Acta 497:641–651 (1977).

Bhuyan, K. C. et al–*Mechanism of Cataractogenesis Induced by 3–amino–1H–1, 2, 4–triazole. I: Morphology and Histopathology of Cataract and the Role of Catalase in the Regulation of H202 in the Eye*, Biochemical and Clinical Aspects of Oxygen, 785–796 (1979).

Clark, A. F.–*Evaluation of Anti–Glaucoma Compounds And Discovery Of Pathogenic Mechanisms Using Perfusion Cultured Human Eyes*, Exp. Eye Res. 55:266 (1992).

Ellis, P. P.–*Basic Considerations (Chap. 1), Therapy of Diseases of the Cornea (Chap. 11), Therapy of Glaucomas (Chap 13)*, Ocular Therapeutics and Pharmacology, pp. 3–27, 137–157, 162–186 (7th ed 1985).

Epstein, D. L.–*Chandler and Grant's Glaucoma*, pp. 3–5, 129–143, 181–183, 191, 194–195, 201–210, 211, 293–294, 311, 320–321, 352–379, 396 and 403–407 (3d ed. 1986).

Flach, A. J.–*Cyclo–oxygenase Inhibitors in Opthalmology*, Survey of Ophthalmology, 36:259–284 (1992).

Fauss, D. J. et al.–*Glucocorticoid (GC) Effects on HTM Cells: Biochemical Approaches and Growth Factor Responses*, Basic Aspects of Glaucoma Research III, pp. 319–330 (1993).

Giblin, F. J. et al.–*The Role of Glutathione Metabolism in the Detoxification of H202 in Rabbit Lens*, Invest. Ophthalmol. Vis. Sci. 22:330–335 (1982).

Huk, B. et al.–*Anti–Inflammatory Treatment after Argon Laser Trabeculoplasty*, Ophthalmologica 203:24–29 (1991).

Insel, P. A. et al.–*Analgesic–Antipyretics and Antiinflammatory Agents; Drugs Employed in the Treatment of Rheumatoid Arthritis and Gout*, Goodman and Gilman's The Pharmacological Basis of Therapeutics, pp. 638–641 (8th ed. 1990).

Kahn, M. G. et al.–*Glutathione in Calf Trabecular Meshwork and its Relation to Aqueous Humor Outflow Facility*, Invest. Ophthalmol. Vis. Sci. 24:1283–1287 (1983).

Klemetti, A.–*The Dexamethason Provocative Test: A Predictive Tool for Glaucoma?*, Acta Ophthalmol. 68:29–33 (1990).

Langer, R.–*Controlled Release of Macromolecules*, Chem. Tech. 12:98–105 (1982).

Lee, V. H. L.–*Review: New Directions in the Optimization of Ocular Drug Delivery*, J. Ocular Pharmacol. 6:157–164 (1990).

Leske, M. C. et al.–*Estimating Incidence from Age–Specific Prevalence in Glaucoma*, Amer. J. Epidemiol. 113:606–613 (1981).

Lombardino, J. G.–*Nonsteroidal Anti–inflammatory Drugs. Chapter Two: Inflammation– Mechanisms and Mediators*, pp. 75–109 (1985).

*McGraw–Hill Encyclopedia of Science and Technology: Eye* (vertebrate) 8:544–552 (6th ed. 1987).

*McGraw–Hill Encyclopedia of Science and Technology: Glaucoma* 8:131–132 (6th ed. 1987).

Mullins, J. D. et al.–*Ophthalmic Preparations*, Remington's Pharmaceutical Sciences, Chap. 86, pp. 1581–1595 (18th ed. 1990).

Nguyen, K. P. et al.–*Hydrogen Peroxide Removal by the Calf Aqueous Outflow Pathway*, Invest. Ophthalmol. Vis. Sci. 29:976–981 (1988).

Nguyen, T. D. et al.–*Glucocorticoid (GC) Effects on HTM Cells: Molecular Biology Approaches*, Basic Aspects of Glaucoma Research III, pp. 330–343 (1993).

Polansky, J. R. et al.–*Cellular Mechanisms Influencing the Aqueous Humor Outflow Pathway*, Principles and Practice of Ophthalmology, Chap. 13, pp. 226–251 (1994).

Polansky, J. R. et al.–*Cellular Injury from Sustained vs. Acute Hydrogen Peroxide Exposure in Cultured Human Corneal Endothelium and Human Lens Epithelium*, CLAO Journal Supp. 16:S23–S29 (1990).

Polansky, J. R. et al.–*Human Trabecular Cells*, Invest. Ophthalmol. Vis. Sci. 18:1043–1049 (1979).

Polansky, J. R. et al.–*Studies on Human Trabecular Cells Propagated in Vitro*, Vision Res. 21:155–160 (1981).

Polansky, J. R. et al.–*In Vitro Correlates of Glucocorticoid Effects on Intraocular Presszure*, Glaucoma Update IV, pp. 20–29 (1991).

Polansky, J. R. et al.–*Eicosanoid Production and Glucocorticoid Regulatory Mechanisms in Cultured Human Trabecular meshwork Cells*, The Ocular Effects of Prostaglandins and other Eicosanoids, pp. 113–138 (1989).

Polansky, J. R.–*Side Effects of Topical Ophthalmic Therapy With Anti–Inflammatory Steroids and B–Blockers*, Current Opinion in Ophthalmology 3:259–272 (1992).

Polansky, J. R. et al.–*Growth Factor Effects and Modulation of Glucocorticoid (GC) and Other Stress Responses in Human Trabecular Meshwork (HTM) Cells*, Experimental Eye Research 55:265 (1992).

Polansky, J. R.–*Basic Pharmacology of Corticosteroids*, Current Topics in Ocular Inflammation, No. 1, pp. 9–21 (1993).

Polansky, J. R. et al.–*HTM Cell Culture Model For Steroid Effects on Intraocular Pressure: Overview*, Basic Aspects of Glaucoma Research III, pp. 307–318 (1993).

Polansky, et al.–*Anti–Inflammatory Agents: Steroids as Anti–Inflammatory Agents*, Handbook of Experimental Pharmacology 69:491–503 (1984).

Polansky, et al.–*Cellular Sensitivity to Glucocorticoids in Patients with POAG*, Investigative Ophthalmology & Visual Science 26:805–809 (1985).

Ringvold, A. et al–*Electron Microscopy of the Trabecular Meshwork in Eyes with Exfoliation Syndrome*, Virchows Arch. Abt. A Path. Anat. 353:110–127 (1971).

Rohen, J. W. et al.–*The Phagocytic Activity of the Trabecular Meshwork Endothelium*, Albrecht v. Graefes Arch. Clin. Exper. Ophthalmol. 175:143–160 (1968).

Shabo, A. L. et al.–*Observations on the Fate of Blood in the Anterior Chamber*, Amer. J. Ophthalmol. 73:25–36 (1972).

Sidman, K. R. et al.–*Controlled Release of Macromolecules and Pharmaceuticals from Synthetic Polypeptides Based on Glutamic Acid*, Biopolymers 22:547–556 (1983).

Snyder, R. W. et al.–*Corticosteroid Treatment and Trabecular Meshwork Proteases in Cell and Organ Culture Supernatants* Exp. Eye Res. 57:461–468 (1993).

Spector, A. et al.–*Hydrogen Peroxide and Human Cataract*, Exp. Eye Res. 33:673–381 (1981).

Strong, N. P.–*How Optometrists Screen for Glaucoma: A Survey*, Ophthal. Physiol. Opt. 12:3–7 (1992).

Trier, K. et al.–*The Use of Estrogens in the Preparation of Formulation For Topical Treatment of High Pressure in the Eyes*, Chemical Abstracts 117:56002d (1992).

Vaughan, D. et al.–*Glaucoma*, General Ophthalmology, Chap. 11, pp. 213–230 (1992).

Weinreb, R. N. et al.–*Prostaglandin Production by Human Trabecular Cells: In Vitro Inhibition by Dexamethasone*, Invest. Ophthalmol. & Vis. Sci. 24:1541–1545 (1983).

Yun, A. J. et al.–*Proteins Secreted by Human Trabecular Cells*, Invest. Ophthalmol. Vis. Sci. 30:2012–2022 (1989).

Zhan, G. et al.–*Steroid Glaucoma: Corticosteroid–induced Ocular Hypertension in Cats*, Exp. Eye Res. 54:211–218 (1992).

Zun, L. S.–*Formulary of Commonly Used Ophthalmologic Medications*, Emerg. Med. Clin. North. Amer. 6:121–126 (1988).

METHODS FOR THE CYTO-PROTECTION OF THE TRABECULAR MESHWORK

FIELD OF THE INVENTION

The present invention is in the field of therapeutics, and concerns methods and reagents for protecting the cells of the trabecular meshwork from agents or processes that would otherwise result in trabecular cell loss. This invention was supported with Government funds (NIH EY02477 and NIH EY 08905-02). The Government has certain rights in this invention.

BACKGROUND OF THE INVENTION

"Glaucomas" are a group of debilitating eye diseases that are the leading cause of blindness subject to positive intervention in the United States and other developed nations. The term "glaucoma" actually encompasses a variety of ophthalmic disease states which are caused by distinct disease processes or pathological conditions of the eye. The disease states under the term "glaucoma" generally share the characteristic of having elevated intraocular pressure ("IOP"), which is a major risk factor in producing visual field loss and blindness. Of the many different ophthalmic disease states, Chandler et al (Glaucoma, 3d Ed., Lea and Febliger, Philadelphia (1986)) describe the following forms: primary open-angle glaucoma ("POAG"), progressive low-tension glaucoma, exfoliation and open-angle glaucoma ("OAG"), amylodosis and open-angle glaucoma, pigment dispersion and pigmentary glaucoma, angle-closure glaucoma, combined open-angle and angle-closure glaucoma, malignant glaucoma, angle-closure glaucoma after scleral buckling operations for separated retina, angle-closure glaucoma due to a multiple cyst of iris and ciliary body, angle-closure glaucoma secondary to occlusion of the central retinal vein, angle-closure glaucoma secondary to bilateral transitory myopia, glaucoma from perforating injuries, glaucoma from contusion of the eye, hemolytic or ghost-cell glaucoma, glaucoma associated with congenital and spontaneous dislocations of the lens, lens-induced glaucoma, glaucoma in aphasia, glaucoma due to intraocular inflammation, neovascular glaucoma, glaucoma associated with extra ocular venous congestion, essential atrophy of the iris with glaucoma, corticosteroid glaucoma, glaucoma after penetrating keratoplasty and characteristically unilateral glaucomas. In almost all cases, the IOP found in these glaucoma syndromes results from an increase in aqueous outflow resistance (see, Vaughan, D. et al., In: *General Ophthamology*, Appleton & Lange, Norwalk, Conn., pp. 213–230 (1992)).

Primary open-angle glaucoma ("POAG"), also termed chronic open-angle glaucoma ("COAG"), is the most prevalent form of glaucoma. The incidence of this condition in persons over the age of forty is about 0.4–0.5%. (Leske, M. C. et al., *Amer. J. Epidemiol.* 113:1843–1846 (1986); Bengtsson, B., *Br. J. Ophthamol.* 73:483–487 (1989); Strong, N. P., *Ophthal. Physiol. Opt.* 12:3–7 (1992)). Moreover, the prevalence of the disease rises with age to over 6% of those 75 years or older (Strong, N. P., *Ophthal. Physiol. Opt.* 12:3–7 (1992)). POAG is characterized by the loss of trabecular meshwork endothelial cells which is associated with degeneration of the normal structure of the trabecular meshwork. This degeneration leads to the obstruction of the normal ability of aqueous humor to leave the eye (see, Vaughan, D. et al, In: *General Ophthamology*, Appleton & Lange, Norwalk, Conn., pp. 213–230 (1992)).

In ordinary terminology, glaucoma is called "primary" if the pathogenic defect is believed to occur primarily within the tissue itself and without an obvious outside causal mechanism which can be defined for "secondary" glaucomas (e.g., see *McGraw-Hill Encyclopedia of Science and Technology*, 6th Ed., Vol. 8, p. 131 (McGraw-Hill 1987). In both POAG (for which no precise cause is known, although toxic substances produced locally and/or from the aqueous humor are believed to account for trabecular cell damage/death) and pigmentary glaucoma (often classified as a secondary glaucoma since the pigment or other debris from the posterior iris is thought to produce damage when engulfed by trabecular meshwork cells) there is known to be a marked loss of the endothelial cells of the meshwork. It is possible that oxidation products play a role in producing damage in the trabecular meshwork in both of these conditions, as well as in ocular iron toxicity, which can also produce a glaucoma. It would be very important to protect trabecular meshwork endothelial cells from injury and death which occurs in the disease processes. A loss in the number of trabecular meshwork cells and alteration in the function of the remaining cells is believed to be responsible for a decrease in the normal ability of aqueous humor to leave the eye, leading to decreased outflow facility (increased outflow resistance), and elevated IOP.

It previously has been demonstrated that aging itself leads to a progressive loss of human trabecular meshwork cells which also eventually leads to a compromise of the meshwork structure over time. Indeed, increased outflow resistance appears to occur in the non-glaucomatous aging population, and a method to preserve the cells in an aging normal individual as well as those with a recognized chronic glaucoma syndrome would be highly desirable. For these reasons, it would be desirable to have a means of treating or preventing pathological changes such as trabecular meshwork endothelial cell loss which are associated with the development and progression of these glaucoma syndromes. The present invention provides such improved therapeutic agents and methods.

Elevated IOP results in progressive visual loss and blindness if not treated appropriately and in a timely fashion. The normal IOP for humans usually measures 10–20 mm Hg (1.3–2.7 kilopascals) and is maintained by a balance between the aqueous inflow and outflow; with rare exceptions, all glaucoma syndromes being associated with an outflow defect. The aqueous humor is produced by the ciliary body in the eye and passes from the posterior chamber through the papillary space into the anterior chamber. The aqueous drains through the trabecular meshwork into Schlemm's canal, through which it leaves the eye. Elevated IOP is considered a major risk factor in producing damage to the optic nerve head, leading to loss of visual fields and eventually to blindness in many patients. Even in so called "normal tension glaucoma," lowering of an apparently normal IOP is thought to help prevent visual loss.

In the currently available treatments for glaucoma, one attempts to symptomatically lower the IOP by decreasing the amount of inflow (decreasing the rate of aqueous formation) or by increasing the facility of outflow. Although outflow can be increased by a variety of drugs, as will be appreciated, the available treatments do not address the underlying pathogenic processes in POAG, pigmentary glaucoma and other syndromes associated with cell loss (nor do they address the trabecular meshwork cell loss associated with normal aging).

Examples of various drug treatments that symptomatically reduce IOP (see, e.g., Babcock, J. C. et al., U.S. Pat.

No. 5,124,154; Epstein, D. L., U.S. Pat. No. 4,757,089; Doulakas, J., U.S. Pat. No. 4,829,088) include: pilocarpine and epheneprine, which owe their effectiveness to increasing the facility of outflow; as well as timolol and other beta blockers, carbonic-anhydrase-inhibiting drugs, and alpha adrenergic agents, which owe their effectiveness to decreasing the rate of formation of aqueous.

Doulakas (U.S. Pat. No. 4,829,088) discloses the use of an ophthalmic medicament containing diclofenac-sodium in aqueous solution for the treatment of inflammations of the eye. Diclofenac-sodium is a non-steroidal anti-inflammatory ("NSAI") agent which is believed to be an alternative to corticosteroids (glucocorticoids) for the treatment of some inflammatory symptoms in the eye, and appears especially useful for the symptomatic relief of pain. The aqueous solution is made suitable for the local treatment of inflammations of the eye due to its stability against chemical decomposition of the diclofenac-sodium and preservation properties and toleration by the eye.

Nagy (U.S. Pat. No. 4,960,799) discloses aqueous ophthalmic solutions containing diclofenac-sodium. The solutions, having a pH of about 7.8, comprise per milliliter of solution about 0.1 to about 5.0 milligrams of (a) pharmaceutically acceptable salt of ortho-(2,6-dichlophenyl-)aminophenyl acetic acid; (b) about 0.1 to about 10 milligrams of a pharmaceutically acceptable sale of ethylene diamine tetraccetic acid, (c) about 0.5 to about 200 milligrams of a pharmaceutically acceptable solubilizer, (d) about 0.01 to about 5.0 milligrams of a pharmaceutically acceptable bacteriostat and (e) the remainder water. The ophthalmic solutions are used for topical administration to the eye for the control or treatment of ocular inflammation.

Cherng-Chyi et al. (U.S. Pat. No. 5,110,493) relates to ophthalmic non-steroidal anti-inflammatory drug formulations containing a quaternary ammonium preservative and a non-ionic surfactant. The formulations are useful for treating diseases that are either caused by, associated with or accompanied by inflammatory processes.

The above, and others in the well-known class of NSAI agents have been proposed to suppress signs of inflammatory responses, to prevent particular side-effects of surgical trauma, especially fluid accumulating in the back of the eye, and the appearance of inflammatory cells and vessel leakage in the anterior chamber. NSAI agents useful in treating inflammation are known to inhibit prostaglandin production and also to affect other eicosanoid pathways. NSAI agents are believed to be a possible alternative for glucocorticoids to reduce inflammation and avoid side-effects due to these drugs (e.g., concealing the risk of deterioration as a result of bacterial or viral infection), but in practice, NSAI agents have proven to be much less effective in treating many different types of ocular inflammation.

There is no NSAI agent that has been proposed to overcome the loss of trabecular cells associated with normal aging, nor in conditions in which cell loss and cell damage appear greater—as in POAG, pigmentary glaucoma and some other glaucoma syndromes. Preventing or treating loss of trabecular cells is particularly important since the IOP control in many glaucomatous patients eventually becomes a problem, which, even with optimal medical and surgical therapy, may lead to progressive visual loss. It also has been demonstrated that aging itself leads to a progressive loss of human trabecular meshwork cells which will eventually lead to a compromise of the meshwork over time. Indeed, increased outflow resistance appears to occur in the non-glaucomatous aging population, and a method to preserve the cells in an aging normal individual as well as those with a recognized chronic glaucoma syndrome would be highly desirable. For these reasons, it would be desirable to have a means of treating or preventing pathological changes such as trabecular meshwork endothelial cell loss which are associated with the development and progression of these glaucoma syndromes. The present invention provides such improved therapeutic agents and methods.

SUMMARY OF THE INVENTION

The invention concerns the recognition that a loss of trabecular cells and loss of the normal structure of the trabecular meshwork contribute to the increased intraocular pressure that characterizes glaucomas.

The invention further concerns the recognition that certain non-steroidal anti-inflammatory agents (in addition to known anti-oxidants, such as vitamin E) produce cytoprotective effects on trabecular cells. Such agents can thus be used, singularly, in combination with other NSAI agents, or in combination with other agents, to prevent or treat the loss of trabecular cells observed in glaucomatous patients.

In detail, the invention provides a method for cytoprotection of the trabecular meshwork, comprising administering to a human a composition including (a) an ophthalmologically effective amount of a non-steroidal cyclooxygenase inhibitor, and (b) a pharmaceutically acceptable carrier, to prevent the loss of trabecular cells.

The invention particularly concerns the embodiment wherein the NSAI agent is selected from the group of known cyclooxygenase inhibitor consisting of salicylates, indoles, phenylalkanoic acids, phenylacetic acids and pyrazolons, or from the group consisting of diclofenac, indomethacin and fenoprofen.

The invention additionally concerns the embodiment wherein the composition is administered topically (as in an aqueous polymeric solution, aqueous suspension, ointment or gel vehicle), or by intraocular injection, oral administration (as with an aqueous solution, aqueous suspension, elixir, tablet, caplet or capsule) and intravenous injection.

The invention additionally provides a method for cytoprotection of the trabecular meshwork, comprising administering to a human a composition including (a) an ophthamologically effective amount of diclofenac, and (b) a pharmaceutically acceptable carrier, including a lightly cross-linked carboxy-containing polymer, in the form of an aqueous polymeric solution, suspension, ointment or gel for topical administration, to prevent the loss of trabecular cells.

The invention additionally provides a method for cytoprotection of the trabecular meshwork, comprising administering to a human in need of treatment or prevention of oxidative injury to its trabecular cells, or of damage to the trabecular cells from phagocytic or endocytic processes or other causes, a composition including (a) an ophthalmically effective amount of a non-steroidal anti-inflammatory cyclooxygenase inhibitor and (b) a pharmaceutically inert carrier, to prevent the loss of trabecular cells.

The invention also provides a composition for cytoprotection of the trabecular meshwork, comprising (a) a nonsteroidal cyclooxygenase inhibitor of a type and in an amount to prevent trabecular cell, and (b) a pharmaceutically acceptable carrier therefor. In particular, the composition contains diclofenac, indomethecin or fenoprofen.

DETAILED DESCRIPTION OF THE INVENTION

I. Overview of the Invention

Human trabecular meshwork (HTM) cells are endothelial-like cells that line the outflow channels by which aqueous humor exits the eye. As indicated above, the trabecular meshwork has been proposed to play an important role in the normal outflow of the aqueous fluid, and has been presumed to be the major site of outflow resistance in glaucomatous eyes.

An increased resistance to outflow through the trabecular meshwork is believed to cause the elevated IOP observed in POAG and other major glaucoma syndromes. The present invention pertains to a recognition that the health and viability of the cells which provide the endothelial lining of the trabecular meshwork structure are essential in preserving the integrity of the outflow channels. A loss in the number and/or function of these cells results in the development of pathological changes which lead to the collapse or covering of the structures of the outflow pathway, or otherwise compromise the normal function of such structure. The result of such changes is the increased outflow resistance observed in POAG and other forms of glaucoma (e.g., pigmentary glaucoma).

The present invention is thus directed to methods for treating trabecular meshwork cells subject to cell loss in order to maintain the number of the trabecular cells. Treatments that protect the viability of cells of the trabecular meshwork from agents or processes that would otherwise cause trabeular cell loss are referred to herein as "cyto-protective" treatments.

As used herein, a treatment is said to have "minor to null" effect if it results in an increase in cytoprotection relative to untreated controls of less than 10%. A treatment is said to have "minimal" effect if it results in an increase in cytoprotection relative to untreated controls of 10–20%. A treatment is said to have "substantial" effect if it results in an increase in cytoprotection relative to untreated controls of between 20–50%. A treatment is said to have "major" effect if it results in an increase in Cytoprotection relative to untreated controls of between greater than 50%.

II. The Cyto-Protection of Trabecular Cells

The cyto-protective treatments of the present invention may be used to protect trabecular cells against loss caused by a diverse set of harmful agents or processes. Examples of such agents and processes include agents that cause oxidative injury, and cell-mediated processes (such as phagocytosis and endocytosis of toxic materials) that have a negative effect on trabecular meshwork cells.

A. Agents and Processes Causing Trabecular Cell Loss

1. Oxidative Injury

Human trabecular meshwork cells encounter relatively high concentrations of hydrogen peroxide and other reactive oxygen species. The stress from these factors has been proposed to result in decreased human trabecular meshwork function, involving loss of trabecular meshwork cells and loss of normal outflow architecture, thereby impeding the outflow of aqueous humor (Polansky, J. R et al., In: *Principles and Practice of Ophthalmology*, pp. 226–247, W. B. Saunders & Company, Philadelphia (1994)). Experiments to test this proposal at first only demonstrated injury if relatively high levels (i.e., >1 mM) of hydrogen peroxide were employed, and if defensive enzymes were inhibited (Bhuyan, K. C. et al., *Biochem. Biophys. Acta* 497:641 (1977); Bhuyan, K. C. et al., In: "Biochemical and Clinical Aspects of Oxygen," Caughey, W. S. (ed.) p. 795 (1981); Spector, A. et al, *Exper. Eye Res* 33:673 (1981); Giblin, F. J. et al., Invest. *Ophthalmol. Vis. Sci.* 22:330 (1982); Kahn, M. G. et al., Invest. *Ophthalmol. Vis. Sci.* 24:1283–1287 (1983)). However, it was later discovered that lower levels of hydrogen peroxide (i.e., 0.05–0.1 mM) can produce noticeable effects in trabecular meshwork cells if the hydrogen peroxide exposure were maintained for 1–2 hours rather than using only a brief exposure (Polansky, J. R., et al., *CLAO suppl.* 16:S23 (1990)).

One aspect of the present invention concerns the recognition that the reduced outflow ability of the meshwork that is observed in glaucomatous patients is caused in part by toxic oxidative agents in the aqueous humor. Such agents induce an oxidative injury or oxidative stress to the trabecular meshwork. Since the meshwork is not in direct light, the main causes of the oxidative injury are stable oxidizing species, such as hydrogen peroxide or lipidhydroperoxides, or their breakdown products (Polansky, J. R. et al., In: Principles and Practice of Ophthalmology, page 226–247, W. B. Saunders & Company, Philadelphia (1994); Bhuyan, K. C. et al., Biochem. Biophys. Acta 497:641–651 (1977); Bhuyan, K. C. et al., In: "Biochemical and Clinical Aspects of Oxygen," Caughey, W. S. (ed.) p. 785–796 (1981); Spector, A. et al., *Exper. Eye Res* 33:673–381 (1981); Giblin, F. J. et al., Invest. *Opthalmol. Vis. Sci.* 22:330–335 (1982); Babizhayev, M. A. et al., Invest. *Opthalmol. Vis. Sci.* 67:371 (1989)).

In this regard, substantial levels of hydrogen peroxide (approximately 0.03 mM) are present in normal aqueous fluid and alterations of normal physiology can significantly increase these levels (Giblin, F. J. et al., Invest. *Opthalmol. Vis. Sci.* 22:330–335 (1982); Kahn, M. G. et al., Invest. *Opthalmol. Vis. Sci.* 24:1283–1287 (1983)). It has been proposed that normal animals detoxify hydrogen peroxide via coupled reactions involving glutathione peroxidase, glutathione reductase and the hexose monophosphate shunt (Giblin, F. J. et al., Invest. *Opthalmol. Vis. Sci.* 22:330–335 (1982)). Catalase is also believed to contol hydrogen peroxide concentration. Processes that impair the capacity of the trabecular meshwork to control peroxide concentration increases the likelihood of oxidative injury (Kahn, M. G. et al., Invest. *Opthalmol. Vis. Sci.* 24:1283–1287 (1983); Nguyen, K. P. V. et al., Invest. *Ophthamol. Vis. Sci.* 29:976–981 (1988)). The trabecular meshwork plays a substantial role in removing excess hydrogen peroxide from the aqueous (Nguyen, K. P. V. et al., Invest. *Ophthamol. Vis. Sci.* 29:976–981 (1988)).

2. Cell-Mediated Injury

Human trabecular meshwork cells are capable of actively attacking debris blocking the outflow channels by both phagocytosis and endocytosis (Polansky, J. R. et al., In: *Principles and Practice of Ophthalmology*, page 226–247, W. B. Saunders & Company, Philadelphia (1994)). As used herein, phagocytosis is the capture and readsorption of cells or major fragments of cellular debris. In contrast, endocytosis is the capture and readsorption of minor fragments of cellular debris, macromolecular complexes, pigment, etc. The phagocytic/endocytic abilities of human trabecular meshwork cells permit them to act as a "self-cleaning filter" (Rohen, J. W. et al., Graefes Arch. *Clin. Exper. Ophthamol.* 175:143 (1968); Ringvoid, A. et al., *Virchows Arch.* [*Pathol. Anat.*] 353:110 (1971); Shabo, A. L. et al., *Amer. J. Ophthamol* 73:25 (1972)).

Although such processes naturally occur, it is believed that phagocytosis of toxic materials released into the anterior chamber cause cell damage and loss. In the course of certain secondary glaucomas (i.e., glaucoma associated with pigment dispersion), the cells of the trabecular meshwork are subjected to excessive phagocytic and/or endocytic attack of materials that become toxic, leading to cell damage and loss.

The endocytosis of pigment associated with cell membrane fragments is believed to have a toxic effect on human trabecular meshwork cells, and this effect appears greater if the membranes have been oxidized in preliminary studies (Polansky, J. R. et al., In: Principles and Practice of Ophthalmology, page 226–247, W. B. Saunders & Company, Philadelphia (1994)).

B. Cyto-Protective Agents

A second aspect of the present invention concerns the recognition that non-steroidal anti-inflammatory ("NSAI") agents are able to counter the effect of such injury, whether due to oxidation or other causes, and to thereby prevent or treat (i.e., slow or minimize) the loss of trabecular meshwork cells. Such agents are able to disrupt the pathogenic processes that cause the reduced outflow facility and elevated IOP of glaucomas. Such agents therefore may be used to treat chronic glaucomas or pigmentary glaucoma that are induced or aggravated by the loss of trabecular meshwork cells.

NSAI agents have been previously used in the eye primarily to treat inflammatory conditions and pain (see, for example, U.S. Pat. Nos. 4,960,799; 4,829,088, 5,110,493). This includes their application as topical agents in the eye, in which their ability to suppress inflammatory responses and to prevent particular side-effects of surgical trauma (on the pupil preventing surgical meiosis), fluid accumulating in the back of the eye after cataract surgery (post-surgical macular edema) and the appearance of inflammatory cells and vessel leakage in the anterior chamber. Topical application of NSAI agents in the eye also appear to relieve some of the itching due to allergic conjunctivitis. These conditions fit in the normal and expected effects of NSAI agents in inflammation and pain. In view of the known mechanisms of action of NSAI agents to lower prostaglandin (and other eicosanoid) production, it is quite surprising that such agents could provide a cyto-protective effect on trabecular meshwork cells, and prevent cell loss. It is especially surprising that a pretreatment of the cells with these agents would prevent subsequent injury even if the drug is not present in the fluid surrounding the cells at the time of injury.

The concept that NSAI agents could be used in the treatment of "inflammatory glaucoma" (i.e., inflammation in the anterior part of the eye (anterior uveitis)) has been previously proposed. In this glaucoma syndrome, it is thought that inflammatory cells from acute inflammation contribute to an elevated IOP which can become very dangerous if not treated. It was proposed, but never proven, that this glaucoma syndrome might be treated by decreasing inflammation with NSAI agents. Because NSAI agents have not been found to have a major effect in treating inflammatory glaucoma, they are not generally used for this condition. Instead, corticosteroids are the drugs of choice to treat inflammation in patients with inflammatory glaucoma; these drugs are used along with palliative measures that help to keep the IOP down, until inflammatory processes are brought under control.

III. The Preferred Agents of the Invention

The preferred agents of the present invention comprise nonsteroidal anti-inflammatory agents that are able to prevent or lessen a damage to, or a loss of, trabecular cells, that is caused by a variety of mechanisms including oxidative injury to the tissues of the eye, and especially to the trabecular meshwork.

One class of NSAI agents that may be used in accordance with the methods of the present invention are "eicosanoid inhibiting agents." Eicosanoid inhibiting agents include those compounds which inhibit prostaglandin and other eicosanoid or cyclooxygenase pathways which are believed to affect IOP. Compounds considered within the classification of eicosanoid inhibitors include certain NSAI agents. The ability of a drug to suppress cyclooxygenase activity and eicosanoid synthesis in model systems does not appear to predict the cyto-protective effects observed.

NSAI agents have been documented by J. Lombardino in *Nonsteroidal Anti-inflammatory Drugs*, Wiley-Interscience, New York, (1985). Examples of compounds of this class of anti-inflammatory drugs include but are not limited to the following: aspirin, benoxaprofen, benzofenac, bucloxic acid, butibufen, carprofen, cicloprofen, cinmetacin, clidanac, clopirac, diclofenac, etodolac, fenbufen, fenclofenac, fenclorac, fenoprofen, fentiazac, flunoxaprofen, furaprofen, flurbiprofen, furobufen, furofenac, ibuprofen, ibufenac, indomethacin, indoprofen, isoxepac, ketoprofen, lactorolac, lonazolac, metiazinic, miroprofen, naproxen, oxaprozin, oxepinac, phenacitin, pirprofen, pirazolac, protizinic acid, sulindac, suprofen, tiaprofenic acid, tolmetin, and zomepirac.

Non-steroidal eicosanoid inhibiting compounds can be prepared in the form of pharmaceutically acceptable salts, esters and other prodrugs. Derivative salts include relatively non-toxic inorganic or organic acid addition salts or alkaline earth metal salts of the therapeutic compounds, which can be prepared in situ during the final isolation and purification of the compounds or by separately reacting the free base with a suitable organic or inorganic acid. Where the compounds include a basic functionality such as amine or alkylamine, representative salts include hydrochloride, sulfate, acetate, maleate, lauryl sulphate, and the like. Where an acidic functionality is present, salts such as sodium, calcium, potassium and magnesium salts may be formed.

Additional examples of NSAI agents include non-narcotic analgesic/non-steroidal anti-inflammatory compounds such as (1) propionic acid derivatives, (2) acetic acid derivatives, (3) fenamic acid derivatives, (4) biphenylcarboxylic acid derivatives and (5) oxicams.

While some of these agents are primarily used at the present time as anti-inflammatory agents and others are primarily used as analgesics, in fact all of the contemplated compounds have both analgesic and anti-inflammatory activity and can be used at appropriate dosage levels for either purpose in various compositions.

The compounds in groups (1) through (4) typically contain a carboxylic acid function; however, those acids are sometimes administered in the form of their pharmaceutically acceptable acid addition or alkali metal salts, e.g., sodium salts.

The propionic acid derivatives include, but are not limited to, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alimoprofen, tiaprofenic acid, fluprofen and bucloxic acid. Structurally related propionic acid derivatives having similar analgesic and anti-inflammatory properties are also intended to be encompassed by this group.

Thus, "propionic acid derivatives" as defined herein are non-narcotic analgesics/non-steroidal anti-inflammatory drugs having a free —CH(CH$_3$)COOH or —CH2CH$_2$COOH group (which optionally can be in the form of a pharmaceutically acceptable salt group, e.g., —CH(CH$_3$)COO$^-$Na$^+$), typically attached directly or via a carbonyl function to a ring system, preferably to an aromatic ring system.

Acetic acid derivatives as defined herein include, but are not limited to, indomethacin, sulindac, tolmetin, zomepirac, diclofenac, fenclofenac, alclofenac, ibufenac, isoxepac, furofenac, tiopinac, zidometacin, acemetacin, fentiazac, clidanac and oxpinac. Structurally related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g., —CH2COO$^-$Na$^+$), typically attached directly to a ring system, preferably to an aromatic or heteroaromatic ring system.

Fenamic acid derivatives as defined herein include, but are not limited to, mefenamic acid, meclofenamic acid, flufenamic acid, niflumic acid and tolfenamic acid. Structurally related fenamic acid derivatives having similar analgesic and anti-inflammatory properties are also intended to be encompassed by this group.

Thus, "fenamic acid derivative" as defined herein are non-narcotic analgesics/non-steroidal anti-inflammatory drugs which contain the basic structure

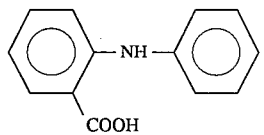

which can bear a variety of substituents and in which the free —COOH group can be in the form of a pharmaceutically acceptable salt group, e.g., —COO$^-$NA$^+$.

The biphenylcarboxylic acid derivatives as defined herein include, but are not limited to, diflunisal and flufenisal. Structurally related biphenylcarboxylic acid derivatives having similar analgesic and anti-inflammatory properties are also intended to be encompassed by this group.

Thus, "biphenylcarboxylic acid derivative" as defined herein are non-narcotic analgesics/non-steroidal anti-inflammatory drugs which contain the basic structure

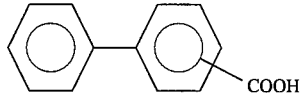

which can bear a variety of substituents and in which the free —COOH group can be in the form of a pharmaceutically acceptable salt group, e.g., —COO$^-$NA$^+$.

The oxicams as defined herein include, but are not limited to, piroxicam, sudoxicam, isoxicam, and CP-14,304. Structurally related oxicams having similar analgesic and anti-inflammatory properties are also intended to be encompassed by this group. A preferred member of this group is piroxicam.

Thus, "oxicams" as defined herein are non-narcotic analgesics/non-steroidal anti-inflammatory drugs which have the general formula:

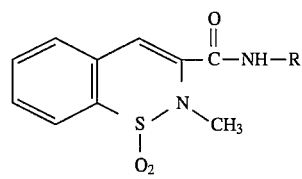

wherein R is an aryl or heteroaryl ring system.

Also included within the non-steroidal eicosanoid inhibitors or NSAI agents of the present invention are certain cyclooxygenase inhibitors as described by Flach, A. J., Survey Ophthalmology 36:259–284 (1992). Cyclo-oxygenase inhibitors are non-steroidal antiinflammatory drugs that have become available as ophthalmic eyedrops for treatment of inflammation. These inhibitors may be grouped into six different classes: salicylates, fenamates, indoles, phenylalkanoic acids and pyrazolones. Specific drugs within the respective groups are summarized below.

| Cyclo-oxygenase Inhibitors | |
| --- | --- |
| Chemical Class | Generic Name |
| Salicylates | Aspirin, Salicylic Acid, Diflunisol |
| Indoles | Indomethacin, Sulinda, Tolmetin |
| Phenylalkanoic acids | Fenoprofen, Flurbiprofen, Ibuprofen, Ketoprofen, Ketorolac, Naproxen, Piroxicam, Suprofen |
| Phenylacetic acids | Diclofenac |
| Pyrazolons | Oxyphenbutazone, Phenylbutazone, Antipyrine, Aminopyrine, Azapropazone |

IV. Methods of Administration

The agents of the present invention can be formulated according to known methods to prepare pharmaceutically acceptable compositions, whereby these materials, or their functional derivatives, having the desired degree of purity are combined in admixture with a physiologically acceptable carrier, excipient, or stabilizer. Such materials are non-toxic to recipients at the dosages and concentrations employed.

A composition is said to be "pharmaceutically acceptable" if its administration can be tolerated by a recipient patient. An agent is physiologically significant if its presence results in a detectable change in the physiology of a recipient patient. Preferably, such compositions are administered topically in an aqueous polymeric solution, aqueous suspension, ointment or gel vehicle.

Suitable vehicles and their formulation, inclusive of other human proteins, e.g., human serum albumin, are described, for example, in Remington's Pharmaceutical Sciences (16th ed., Osol, A., Ed., Mack, Easton Pa. (1980)).

If the composition is to be water soluble, it may be formulated in a buffer such as phosphate or other organic acid salt preferably at a pH of about 7 to 8. If the composition is only partially soluble in water, it may be prepared as a microemulsion by formulating it with a nonionic surfactant such as Tween, Pluronics, or PEG, e.g., Tween 80, in an amount of, for example, 0.04–0.05% (w/v), to increase its solubility. The term "water soluble" as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K or Cs salts.

Optionally other ingredients may be added such as antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinyl pyrrolidone; amino acids, such as glycine, glutamic acid, aspirin, or arginine; monosaccharides, disaccharides, and other carbohydrates including cellulose or its derivatives, glucose, mannose, or dextrins; chelating agents such as EDTA; and sugar alcohols such as mannitol or sorbitol.

Additional pharmaceutical methods may be employed to control the duration of action. Controlled or sustained release preparations may be achieved through the use of polymers to complex or absorb the molecule(s) of the composition. The controlled delivery may be exercised by selecting appropriate macromolecules (for example, polyesters, polyamino acids, polyvinyl pyrrolidone, ethylenevinylacetate, methylcellulose, carboxymethylcellulose, or protamine sulfate) and the concentration of macromolecules as well as the methods of incorporation in order to control release.

Sustained release formulations may also be prepared, and include the formation of microcapsular particles and implantable articles. For preparing sustained-release compositions, the molecule(s) of the composition is preferably incorporated into a biodegradable matrix or microcapsule. A suitable material for this purpose is a polylactide, although other polymers of poly-(α-hydroxycarboxylic acids), such as poly-D-(–)-3-hydroxybutyric acid (EP 133,988A), can be used. Other biodegradable polymers include poly(lactones), poly(orthoesters), polyamino acids, hydrogels, or poly(orthocarbonates) poly(acetals). The polymeric material may also comprise polyesters, poly(lactic acid) or ethylene vinylacetate copolymers. For examples of sustained release compositions, see U.S. Pat. No. 3,773,919, EP 58,481A, U.S. Pat. No. 3,887,699, EP 158,277A, Canadian Patent No. 1176565, Sidman, U. et al., *Biopolymers* 22:547 (1983), and Langer, R. et al, *Chem. Tech.* 2:98 (1982).

Alternatively, instead of incorporating the molecule(s) of the composition into polymeric particles, it is possible to entrap these materials in microcapsules prepared for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

In an alternative embodiment, liposome formulations and methods that permit intracellular uptake of the molecule will be employed. Suitable methods are known in the art, see, for example, Chicz, R. M. et al. (PCT Application WO 94/04557), Jaysena, S. D. et al. (PCT Application WO93/12234), Yarosh, D. B. (U.S. Pat. No. 5,190,762), Callahan, M. V. et al. (U.S. Pat. No. 5,270,052) and Gonzalezro, R. J. (PCT Application 91/05771), all herein incorporated by reference.

The pharmaceutical compositions of the present invention may be sterilized, as by filtration through sterile filtration membranes (e.g., 0.2 micron membranes). The compositions may be stored in lyophilized form or as a liquid solution. It will be understood that use of certain of the foregoing excipients, carriers, or stabilizers will result in the formation of salts of the molecules.

The compositions of the present invention can be applied topically as to the skin, or to the cornea. When applied topically, the molecule(s) of the composition may be suitably combined with other ingredients, such as carriers and/or adjuvants. There are no limitations on the nature of such other ingredients, except that they must be pharmaceutically acceptable and efficacious for their intended administration, and cannot degrade the activity of the active ingredients of the composition. Examples of suitable vehicles include ointments, creams, gels, or suspensions, with or without purified collagen. The compositions also may be impregnated into transdermal patches, and bandages, preferably in liquid or semi-liquid form.

For obtaining a gel formulation, the molecule(s) of the composition formulated in a liquid composition may be mixed with an effective amount of a water-soluble polysaccharide or synthetic polymer such as polyethylene glycol to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, non-toxic, simple to prepare, and not too runny or viscous, and will not destabilize the molecule(s) held within it. Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight polyethylene glycols to obtain the proper viscosity. For example, a mixture of a polyethylene glycol of molecular weight 400–600 with one of molecular weight 1500 would be effective for this purpose when mixed in the proper ratio to obtain a paste.

The compositions of the present invention can also be formulated for administration parenterally by injection, rapid infusion, nasopharyngeal absorption (intranasopharangeally), dermoabsorption, or orally. The compositions may alternatively be administered intramuscularly, or intravenously. Compositions for parenteral administration include sterile aqueous or nonaqueous solutions, suspensions, and emulsions. Examples of nonaqueous solvents are propylene glycol, polyethylene glycol, vegetable oils such as olive oil, and injectable organic esters such as ethyl oleate. Carriers, adjuncts or occlusive dressings can be used to increase tissue permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include wetting agents, emulsifying and suspending agents, or sweetening, flavoring, coloring or perfuming agents. Alternative oral formulations include an aqueous solution, aqueous suspension, elixir, tablet, caplet or capsule.

If methylcellulose is employed in the gel, preferably it comprises about 2–5%, more preferably about 3%, of the gel and the molecule(s) of the composition is present in an amount of about 300–1000 µg per ml of gel. The dosage to be employed is dependent upon the factors described above. As a general proposition, the molecule(s) of the composition is formulated and delivered to the target site or tissue at a dosage capable of establishing in the tissue a maximum dose that is efficacious but not unduly toxic.

In the most preferred embodiment, the molecules of the invention will be provided to the cornea or surface of the eye, and permitted to absorb across the cornea into the anterior chamber of the eye. Methods that may be used for accomplishing such ocular drug delivery are described by Zun, L. S. (*Emerg. Med. Clin. North. Amer.* 6:121 (1988)), Lee, V. H. (*J. Ocular Pharmacol.* 6:157 (1990)), Ellis, P. P. (In: *Ocular Therapeutics and Pharmacology*, 7th ed., Mosby, (1987)), Jannsen, H. J. (U.S. Pat, 5,200,453), Chandrasekaran, S. K. et al. (PCT Appln. No. WO89/06964) and (Vaughan, D. et al., In: *General Ophthamology*, Appleton & Lange, Norwalk, Conn., pp. 213–230 (1992)).

Most preferably, however, such drug administration will be accomplished by combining effective amounts of the agents of the invention with any of the sustained release ophthalmic delivery systems described by Davis, J. P. et al. (U.S. Pat. No. 5,192,535, herein incorporated by reference).

Such preferred sustained release topical ophthalmic medicament delivery systems comprise an aqueous suspension at a pH of from about 3 to about 6.5 and an osmotic pressure of from about 10 to about 400 mOsM containing from about 0.1% to about 6.5% by weight, based on the total weight of the suspension, of a carboxyl-containing polymer prepared by polymerizing one or more carboxyl-containing monoethylenically unsaturated monomers and less than about 5% by weight of a crosslinking agent, such weight percentages of monomers being based on the total weight of monomers polymerized. Desirably the polymer is prepared by suspension or emulsion polymerizing the monomer with the crosslinking agent to a particle size of not more than about 50 µm, preferably not more than about 30 µm, in equivalent spherical diameter. The suspension has an initial viscosity of from about 1,000 to about 30,000 centipoises (cp) and is administrable to the eye in drop form at that initial viscosity. The polymer has average particle size of not more than about 50 µm, preferably not more than about 30 µm, in equivalent spherical diameter. In general, such polymers will range in molecular weight estimated to be about 250,000 to about 4,000,000, and preferably about 500,000 to about 2,000,000.

Aqueous suspensions containing polymer particles prepared by suspension or emulsion polymerization whose average dry particle size is appreciably larger than about 50 µm in equivalent spherical diameter are less comfortable when administered to the eye than suspensions otherwise identical in composition containing polymer particles whose equivalent spherical diameters are, on the average, below about 50 µm. Moreover, above the average 50 µm size, the advantage of substantially increased viscosity after administration is not realized.

The lightly crosslinked suspension is administrable in drop form, upon contact of the lower pH suspension with the higher pH tear fluid of the eye, the suspension is rapidly gellable to a substantially greater viscosity than the viscosity of the suspension as originally administered in drop form. Accordingly, the resulting more viscous gel can remain in the eye for a prolonged period of time so as to release its NSAI agent over a prolonged time period.

A preferred drug delivery system employs a polymer that is preferably prepared from at least about 50% by weight, more preferably at least about 90% by weight, of one or more carboxyl-containing monoethylenically unsaturated monomers. Acrylic acid is the preferred carboxyl-containing, monoethylenically unsaturated monomer, but other unsaturated, polymerizable carboxyl-containing monomers, such as methacrylic acid, ethacrylic acid, β-methylacrylic acid (crotonic acid), cis-β-methylcrotonic acid (angelic acid), trans-α-methylcrotonic acid (tiglic acid), α-butylcrotonic acid, α-phenylacrylic acid, benzylacrylic acid, α-cyclohexylacrylic acid, β-phenylacrylic acid (cinnamic acid), coumaric acid (o-hydroxycinnamic acid), p-hydroxycoumaric acid (umbellic acid), and the like can be used in addition to or instead of acrylic acid. Carbopol 976 and polycarbophil (Davis, et al., U.S. Pat. 5, 192,535) are examples of suitable polymers.

Such polymers are crosslinked by using a small percentage, i.e., less than about 5%, such as from about 0.5% or from about 0.1% to about 5%, and preferably from about 0.2% to about 1%, based on the total weight of monomers present, of a polyfunctional crosslinking agent. The crosslinking agents of such compositions include non-polyalkenyl polyether difunctional crosslinking monomers such as divinyl glycol; 2,3-dihydroxyhexa-1,5-diene; 2,5-dimethyl-1,5-hexadiene; divinylbenzene; N,N-diallylacrylamide; N,N-diallylmethacrylamide and the like. A preferred crosslinking agent is divinyl glycol. Also included are polyalkenyl polyether crosslinking agents containing two or more alkenyl ether groupings per molecule, preferably alkenyl ether groupings containing terminal $H_2C=C<$ groups, prepared by etherifying a polyhydric alcohol containing at least four carbon atoms and at least three hydroxyl groups with an alkenyl halide such as allyl bromide or the like, e.g., polyallyl sucrose, polyallyl pentaerythritol, or the like; see, e.g., Brown, U.S. Pat. No. 2,798,053. Diolefinic non-hydrophilic macromeric crosslinking agents having molecular weights of from about 400 to about 8,000, such as insoluble di- and polyacrylates and methacrylates of diols and polyols, diisocyanate-hydroxyalkyl acrylate or methacrylate reaction products, and reaction products of isocyanate terminated prepolymers derived from polyester diols, polyether diols or polysiloxane diols with hydroxyalkyl-methacrylates, and the like, can also be used as the crosslinking agents; see, e.g., Mueller et al, U.S. Pat. Nos. 4,192,827 and 4, 136,250.

In a preferred method of preparing sustained release topical ophthalmic delivery systems, the foregoing suspensions are prepared and packaged at the desired viscosity of from 1,000 to about 30,000 centipoises, for administration to the eye in drop form. In a preferred delivery method, the foregoing suspensions, containing the medicament, are administered to the eye at the initial viscosity in drop form to cause the administered suspension, upon contact with the higher pH tear fluid of the eye, to rapidly gel in situ to a substantially greater viscosity than the viscosity of the suspension as originally administered in drop form. The more viscous gel remains in the eye for a prolonged period of time so as to release the medicament, entrapped in the more viscous gel formed in the eye, in sustained fashion.

It may be desirable to replace up to about 40% by weight of the carboxyl-containing monoethylenically unsaturated monomers by one or more non-carboxyl-containing monoethylenically unsaturated monomers containing only physiologically and ophthamologically innocuous substituents.

The desired osmotic pressure is preferably achieved by using a physiologically and ophthalmologically acceptable salt in an amount of from about 0.01% to about 1% by weight, based on the total weight of the suspensions. A preferred salt is sodium chloride.

Generally, the dosage needed to provide an effective amount of the composition will vary depending upon such factors as the recipient's age, condition, sex, and extent of disease, if any, and other variables, and can be adjusted and determined by one of ordinary skill in the art. Effective amounts of the compositions of the invention can vary from 0.01–1,000 mg/ml per dose or application, although lesser or greater amounts can be used. For ophthalmic suspensions, the effective amounts will preferably be from about 0.0001% to about 10% by weight, and most preferably from about 0.01% to about 5% by weight, based on the total weight of the suspension.

For example, to provide cyto-protection for the trabecular meshwork of a human, and prevent the loss of trabecular cells, the composition of an ophthalmologically effective amount of a non-steroidal cyclooxygenase inhibitor, and a pharmaceutically acceptable carrier contains between about 0.001% and about 10% by weight amount of the non-steroidal cyclooxygenase inhibitor. The same compositions can be used to provide cyto-protection of the trabecular meshwork in humans in need of treatment or prevention of oxidative injury to its trabecular cells, or of damage to trabecular cells from phagocytic or endocytic processes. Most preferably, for either use, the composition is administered to provide a concentration of inhibitor of less than about $1 \times 10^{-5}$M (and preferably between about $1 \times 10^{9}$M and about $1 \times 10^{-5}$M) in the aqueous humor of the eye.

Having now generally described the invention, the same will be more readily understood through reference to the following examples which are provided by way of illustration, and are not intended to be limiting of the present invention, unless specified.

EXAMPLE 1

Oxidative Stress To

Human Trabecular Meshwork Cells

Confluent monolayers of human trabecular meshwork cells were prepared using conventional methods (Polansky, J. R. et al., Invest. *Ophthamol. Vis. Sci.* 18:1043 (1979); Alvarado, J. A. et al., Invest. *Ophthamol. Vis. Sci.* 23:464 (1982); Polansky, J. R. et al., *Proc. Int. Soc. Eye Res.* 3:76 (1980); Polansky, J. R. et al., *Vision Res.* 21:155 (1981); Polansky, J. R. et al., In: Principles and Practice of Ophthalmology, page 226–247, W. B. Saunders & Company, Philadelphia (1994). Monolayers were exposed to varying concentrations of hydrogen peroxide and other oxidants for their effects on human trabecular meshwork cell morphology and growth following trypsinization.

Morphological changes included an increase in detached cells and the appearance of dark granules in the cytoplasm if hydrogen peroxide levels were maintained at approximately 0.3–1 mM for 1–2 hours. A shorter exposure or a decreased concentration was required to inhibit the growth of trabecular meshwork cells.

When non-steroidal anti-inflammatory agents are provided to cells subjected to oxidative injury, they were found to produce cyto-protective effects in preventing these changes. The protective effects appear to be relatively cell-type specific based upon comparisons between human trabecular meshwork cells, ciliary epithelium, and retinal pigment epithelial cells.

EXAMPLE 2

Peroxide Effect on Protein Secretion by Cultured Trabecular Meshwork Cells

The effect of hydrogen peroxide concentration on the capacity of cultured trabecular meshwork cells to secrete protein was investigated.

Human trabecular meshwork cells were cultured as described in Example 1.

The cells were then provided with aspirin, vitamin E, basic fibroblast growth factor (bFGF), ibuprofin, or tylenol (all at $10^{-5}$M) over a three day period; the media was then changed and the cells exposed to 0.3 mM hydrogen peroxide for 1 hour. After a 24 hour recovery period the amount of secreted protein was measured by assaying the extracellular radioactivity following a 2 hour $^{35}$S-methionine incorporation. The results of this experiment demonstrated that hydrogen peroxide had a profound inhibitory effect on the capacity of human trabecular meshwork cells to secrete protein. This inhibitory effect could be prevented by the presence of aspirin, Vitamin E, ibuprofin or tylenol, but not by bFGF.

EXAMPLE 3

Effect of NSAI Agents on Uptake of Rb by Cultured Trabecular Meshwork Cells Subjected to Oxidative Stress The effect of NSAI agents on the capacity of cultured trabecular meshwork cells exposed to oxidative injury to incorporate Rb was investigated.

Human trabecular cells were treated on both three and one days prior to oxidative stress with aspirin, diclofenac, Vitamin E acetate, fenoprofen, flurbiprofen, ibuprofen, indomethacin, phenacetin, tolmetin, and acetaminophen. Solutions were prepared as 50 mM solutions in ethanol, diluted further in culture media and added as 100X dilutions. Oxidative stress was done by first rinsing the cells with 37° C. phosphate buffered saline (PBS) and then adding PBS or 0.6 mM $H_2O_2$ diluted with PBS. The cells were then placed in a 37° C. water-jacketed incubator. After 1 hour, the cells were then changed back to their normal culture media. The following day, the culture media was removed and replaced with $^{86}$RbCl (1 µCi/ml) diluted in PBS with 1 g/l glucose. After incubation at 37° C. for 20 minutes, the rubidium (Rb) solution was removed, the cells rinsed twice with ice cold PBS and the cells were then lysed with 0.1M NaOH. The lysed cells were then counted using a scintillation counter. Table 1 gives the amount of rubidium incorporation for 1 µM and 10 µM drug treatments; control had no drug. Table 1 provides the $^{86}$Rb uptake of treated cells relative to that of the control, expressed as a percentage of the control. As shown, human trabecular meshwork cells pretreated with diclofenac, fenoprofen, flurbiprofen, indomethacin and tolmetin had essentially normal ability to incorporate rubidium.

TABLE 1

| Drug Pre-Treatment | Conc. (μM) | % Relative $^{86}$Rb Uptake (cpm) 0 mM H$_2$O$_2$ | 0.6 mM H$_2$O$_2$ |
|---|---|---|---|
| Control | 0 | 100 | 10 |
| Aspirin | 1 | | 18 |
| Aspirin | 10 | | 92 |
| Diclofenac | 1 | | 83 |
| Diclofenac | 10 | | 80 |
| Vitamin E Acetate | 1 | | 20 |
| Vitamin E Acetate | 10 | | 20 |
| Fenoprofen | 1 | | 78 |
| Fenoprofen | 10 | | 75 |
| Flurbiprofen | 1 | | 83 |
| Flurbiprofen | 10 | | 89 |
| Ibuprofen | 1 | | 13 |
| Ibuprofen | 10 | | 68 |
| Indomethacin | 1 | | 82 |
| Indomethacin | 10 | | 81 |
| Phenacetin | 1 | | 7 |
| Phenacetin | 10 | | 9 |
| Tolmetin | 1 | | 67 |
| Tolmetin | 10 | | 86 |
| Acetaminophen | 1 | | 6 |
| Acetaminophen | 10 | | 6 |

EXAMPLE 4

Effect of Different Concentration of NSAI Agents on Uptake of Rb by Cultured Trabecular Meshwork Cells Subjected to Oxidative Stress The effect of NSAI agents on the capacity of cultured trabecular meshwork cells to incorporate Rb was investigated.

Human trabecular cells were treated on both three and one days prior to oxidative stress with aspirin, diclofenac, Vitamin E acetate, fenoprofen, flurbiprofen, ibuprofen, indomethacin and acetaminophen. Solutions were prepared as 50 mM solutions in ethanol, diluted further in culture media and added as 100X dilutions. Oxidative stress was done by first rinsing the cells with 37° C. PBS and then adding PBS or 0.6 mM H$_2$O$_2$ diluted with PBS. The cells were then placed in a 37° C. water-jacketed incubator. After 1 hour, the cells were then changed back to their normal culture media. The following day, the culture media was removed and replaced with $^{86}$RbCl (1μCi/ml) diluted in PBS with 1 g/l glucose. After incubation at 37° C. for 20 minutes, the rubidium solution was removed, the cells rinsed twice with ice cold PBS and the cells then were lysed with 0.1M NaOH. The lysed cells were then counted in a scintillation counter. Ther results of the experiment are shown in Table 2. Table 2 shows the $^{86}$Rb uptake of treated cells expressed as a percentage of the uptake of control cells. As shown in Table 2, rubidium uptake for the 1 μM pretreatments of diclofenac and flurbiprofen were at essentially the same levels. However, substantial differences were found for the pretreatments with 0.1 and 0.01 μM diclofenac and flurbiprofen.

It was a particularly unexpected discovery that diclofenac worked at a very low dose in the assays, suggesting that substantially lower doses of topical (and perhaps even systemic) diclofenac, as well as other non-steroidal agents, may prevent the progression of elevated intra-ocular pressure due to loss of and/or injury to trabecular meshwork cells.

TABLE 2

| Drug Pre-Treatment | Conc. (μM) | % Relative $^{86}$Rb Uptake (cpm) H$_2$O$_2$ Concentration | | |
|---|---|---|---|---|
| | | 0 mM | 0.6 mM | 1.0 mM |
| Control | | 100 | 2 | 4 |
| Aspirin | 1 | | 8 | 7 |
| Diclofenac | 0.01 | | 81 | 69 |
| Diclofenac | 0.1 | | 91 | 76 |
| Diclofenac | 1 | | 94 | 88 |
| Vitamin E Acetate | 1 | | 2 | 3 |
| Fenoprofen | 0.1 | | 4 | 3 |
| Fenoprofen | 1 | | 15 | 39 |
| Flurbiprofen | 0.01 | | 7 | 3 |
| Flurbiprofen | 0.1 | | 9 | 18 |
| Flurbiprofen | 1 | | 87 | 81 |
| Ibuprofen | 1 | | 13 | 14 |
| Indomethacin | 1 | | 98 | 92 |
| Acetaminophen | 1 | | 22 | 21 |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for cyto-protection of the trabecular meshwork comprising administering to a human a composition including (a) an ophthalmologically effective amount of a non-steroidal cyclooxygenase inhibitor, and (b) a pharmaceutically acceptable carrier, to prevent the loss of trabecular cells.

2. The method according to claim 1, wherein said cyclooxygenase inhibitor is selected from the group consisting of salicylates, indoles, phenylalkanoic acids, phenylacetic acids and pyrazolons.

3. The method according to claim 1, wherein said non-steroidal cyclooxygenase inhibitor is selected from the group consisting of diclofenac, indomethacin and fenoprofen.

4. The method according to claim 1, wherein said composition is administered topically in an aqueous polymeric solution, aqueous suspension, ointment or gel vehicle.

5. The method according to claim 1, wherein said composition comprises between about 0.001% and about 10% by weight of said cyclooxygenase inhibitor.

6. The method according to claim 5, wherein said composition comprises between about 0.001% and about 0.009% by weight of said inhibitor.

7. The method according to claim 1, wherein said composition is administered to provide a concentration of said inhibitor of less than about $1 \times 10^{-5}$M in the aqueous humor of the eye.

8. The method according to claim 7, wherein said composition is administered to provide a concentration of said inhibitor of between about $1 \times 10^{-9}$M and about $1 \times 10^{-5}$M in the aqueous humor of the eye.

9. The method according to claim 1, wherein said composition is administered by a method selected from the group consisting of intraocular injection, oral administration and intravenous injection.

10. The method according to claim 9, wherein said composition is administered orally, and wherein the composition is an aqueous solution, aqueous suspension, elixir, tablet, caplet or capsule.

11. A method for cyto-protection of the trabecular meshwork, comprising administering to a human a composition including (a) an ophthamologically effective amount of diclofenac, and (b) a pharmaceutically acceptable carrier, including a lightly cross-linked carboxy-containing polymer, in the form of an aqueous polymeric solution, suspension, ointment or gel for topical administration, to prevent the loss of trabecular cells.

12. The method according to claim 11, wherein said diclofenac is present in said formulation in an amount from about 0.001% to about 10% by weight of the composition.

13. The method according to claim 12, wherein said diclofenac is present in said formulation in an amount from about 0.001% to about 0.009% by weight of the composition.

14. The method according to claim 13, wherein said composition is administered in an amount sufficient to provide an ophthalmically effective amount of said diclofenac not exceeding $1\times10^{-5}$M in the aqueous humor of the eye.

15. A method for cyto-protection of the trabecular meshwork, comprising administering to a human in need of treatment or prevention of oxidative injury to its trabecular cells, or of damage to said trabecular cells from phagocytic or endocytic processes, a composition including (a) an ophthalmically effective amount of a non-steroidal anti-inflammatory cyclooxygenase inhibitor and (b) a pharmaceutically inert carrier, to prevent the loss of trabecular cells.

16. The method according to claim 15, wherein said nonsteroidal anti-inflammatory cyclooxygenase inhibitor is selected from the group consisting of salicylates, indoles, phenylalkanoic acids, phenylacetic acids and pyrazolons.

17. The method according to claim 15, wherein said non-steroidal anti-inflammatory cyclooxygenase inhibitor is selected from the group consisting of diclofenac, indomethacin and fenoprofen.

18. The method according to claim 15, wherein said non-steroidal anti-inflammatory cyclooxygenase inhibitor is diclofenac.

19. The method according to claim 15, wherein said composition is administered topically in an aqueous polymeric solution, aqueous suspension, ointment or gel vehicle.

20. The method according to claim 15, wherein said composition comprises between about 0.001 and about 10% by weight of said eicosanoid inhibitor.

21. The method according to claim 20, wherein said composition comprises between about 0.001% and about 0.009% by weight of said inhibitor.

22. The method according to claim 21, wherein said composition is administered to provide a concentration of said inhibitor of less than about $1\times10^{-5}$M in the aqueous humor of the eye.

23. The method according to claim 22, wherein said composition is administered to provide a concentration of said inhibitor of between about $1\times10^{-9}$M and about $1\times10^{-5}$M in the aqueous humor of the eye.

24. The method according to claim 15, wherein said composition is administered by a method selected from the group consisting of intraocular injection, oral administration and intravenous injection.

25. The method according to claim 24, wherein said composition is administered orally, and wherein the composition is an aqueous solution, aqueous suspension, elixir, tablet, caplet or capsule.

26. A composition for cyto-protection of the trabecular meshwork, comprising (a) an opthalmically effective amount of between about 0.001 and about 0.009% by weight of a non-steroidal cyclooxygenase inhibitor of a type and in an amount to prevent trabecular cell damage or loss, and (b) a pharmaceutically acceptable carrier therefor.

27. The composition according to claim 26, wherein said cyclooxygenase inhibitor is diclofenac, indomethecin or fenoprofen.

28. The composition according to claim 27, wherein said cyclooxygenase inhibitor is diclofenac.

29. The method of claim 15, wherein said human is in need of treatment or prevention of oxidative injury to its trabecular cells.

30. The method of claim 29, wherein said oxidative injury is caused by hydrogen peroxide or lipidhydroperoxide.

31. The method of claim 15, wherein said human is in need of treatment or prevention of damage to its trabecular cells from phagocytic or endocytic processes.

* * * * *